United States Patent
Ross (10) Patent No.: US 6,512,536 B1
(45) Date of Patent: Jan. 28, 2003

(54) CABLE AND LINE INSPECTION MECHANISM

(75) Inventor: Terence J. Ross, Rockledge, FL (US)

(73) Assignee: The United States of America as represented by the United States National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 09/257,135

(22) Filed: Feb. 9, 1999

(51) Int. Cl.$^7$ .......................... H04N 7/18; G01B 11/02
(52) U.S. Cl. .......................... 348/61; 356/640; 348/84
(58) Field of Search .......................... 348/61, 82, 84, 348/552, 91; 390/870.07; 356/640; 376/245; 254/287, 333, 134, 3 R (56) References Cited

U.S. PATENT DOCUMENTS

| | | | |
|---|---|---|---|
| 3,775,612 A | | 11/1973 | Foster et al. |
| 3,784,740 A | * | 1/1974 | Copland ....................... 348/84 |
| 3,885,091 A | * | 5/1975 | Fish et al. ..................... 348/84 |
| 3,949,969 A | * | 4/1976 | Kaufer ......................... 254/333 |
| 4,063,711 A | * | 12/1977 | Orihara ........................ 254/134 |
| 4,074,938 A | * | 2/1978 | Taylor ......................... 356/640 |
| 4,557,465 A | * | 12/1985 | Lundberg ..................... 254/287 |
| 4,560,931 A | | 12/1985 | Murakami et al. |
| 4,661,308 A | * | 4/1987 | Takenaka .................... 376/245 |
| 4,818,990 A | * | 4/1989 | Fernandes ............... 340/870.07 |
| RE33,160 E | | 2/1990 | Guthrie et al. |
| 4,904,996 A | * | 2/1990 | Fernandes ............... 340/870.07 |
| 4,964,059 A | | 10/1990 | Sugaya et al. |
| 5,084,764 A | * | 1/1992 | Day ............................. 348/84 |
| 5,118,195 A | | 6/1992 | Dobbie |
| 5,127,726 A | | 7/1992 | Moran |
| 5,203,646 A | | 4/1993 | Landsberger et al. |
| 5,467,640 A | | 11/1995 | Salinas |
| 5,475,441 A | * | 12/1995 | Parulski et al. ............. 348/552 |
| 5,585,707 A | | 12/1996 | Thompson et al. |
| 5,652,617 A | | 7/1997 | Barbour |

* cited by examiner

Primary Examiner—Chris Kelley
Assistant Examiner—Allen Wong
(74) Attorney, Agent, or Firm—Randall M. Heald; Gary G. Borda; John G. Mannix (57) ABSTRACT

An automated cable and line inspection mechanism visually scans the entire surface of a cable as the mechanism travels along the cable=s length. The mechanism includes a drive system, a video camera, a mirror assembly for providing the camera with a 360 degree view of the cable, and a laser micrometer for measuring the cable=s diameter. The drive system includes an electric motor and a plurality of drive wheels and tension wheels for engaging the cable or line to be inspected, and driving the mechanism along the cable. The mirror assembly includes mirrors that are positioned to project multiple images of the cable on the camera lens, each of which is of a different portion of the cable. A data transceiver and a video transmitter are preferably employed for transmission of video images, data and commands between the mechanism and a remote control station.

19 Claims, 6 Drawing Sheets

CABLE AND LINE INSPECTION MECHANISM

ORIGIN OF THE INVENTION

The invention described herein was made by an employee of the United States Government and may be manufactured and used by or for the Government for Government purposes without the payment of any royalties thereon or therefor.

BACKGROUND OF THE INVENTION

The present invention relates in general to an automated mechanism for optically inspecting cables, lines and the like.

The launch pads at Kennedy Space Center employ emergency egress systems in which slidewire cables and baskets are utilized to permit astronauts to descend quickly and safely away from the launch vehicle in case of an emergency. Periodic inspections of the cables are necessary to insure that failures have not occurred which could jeopardize safety. Cable failures are characterized by frayed or jammed strands, bird caging, stretching and corrosion. Inspection crews have been employed in the past to inspect the cables visually as they are lowered down the cables at a controlled speed in a slidewire basket. However, human application of tactile and visual senses in this manner limits the data obtained during the inspections to pass or fail indications. In addition, this operation is obviously hazardous, man intensive and time consuming. An alternative cable inspection technique that overcomes these drawbacks is therefore needed.

SUMMARY OF THE INVENTION

The present invention fulfills the foregoing need through provision of an automated cable and line inspection mechanism that visually scans the entire circumference of a cable or line as the mechanism travels along the length thereof without operator assistance. The mechanism includes a drive system, a video camera and a mirror assembly for providing the camera with a 360 degree view of the cable. These elements are mounted on a frame that can be attached to a cable or line to be inspected with drive and tension wheels in the drive system that engage the cable. An electric motor rotates the drive wheels, thereby driving the mechanism along the cable.

The mirror assembly includes first and second mirrors that are positioned facing portions of the cable that are facing away from the camera lens so that three parallel images of the cable are simultaneously supplied to the camera lens, each of which is of a different section of the cable. This enables the entire circumference of the cable to be imaged without rotational scanning of the camera around the cable.

Other sensing devices are also employed in the preferred embodiment. These include a laser micrometer that measures the diameter of the cable so that it may be determined whether the cable has stretched to an unacceptable degree. A position encoder is also employed to provide an indication of the position along the length of the cable where the cable image is being obtained at any given instant. This enables the location of any noted failures in the cable to be readily determined. Limit switches are also provided to sense when the mechanism has reached the far end of a cable or line, so that the drive motor can be reversed to send the mechanism back to its starting point, where the mechanism can be retrieved.

The video images generated by the video camera are combined with overlaid information, such as the cable diameter and position, and are stored in an on board video storage device, such as a VCR, for later review and analysis. In the preferred embodiment, the images are also transmitted with a video transmitter to a remote control station. In addition, an RF transceiver is employed to enable commands and other data to be communicated between a processor on the cable and line inspection mechanism and the remote control station.

BRIEF DESCRIPTION OF THE DRAWINGS

The features and advantages of the present invention will become apparent from the following detailed description of a preferred embodiment thereof, taken in conjunction with the accompanying drawings, in which.

DETAILED DESCRIPTION OF A PREFERRED EMBODIMENT

With reference to FIGS. 1–5, a cable and line inspection mechanism (CLIM) 10 is illustrated for visually inspecting a cable or line 12 (see FIG. 2) in accordance with a preferred embodiment of the present invention. The CLIM 10 includes a frame 14, to which are mounted, a number of elements. As best illustrated in the schematic illustration of FIG. 2, several of the key elements include a video camera 16, a mirror assembly 18, a laser micrometer 20 for measuring the diameter of the cable 12, and a drive system 22.

Figure 1:
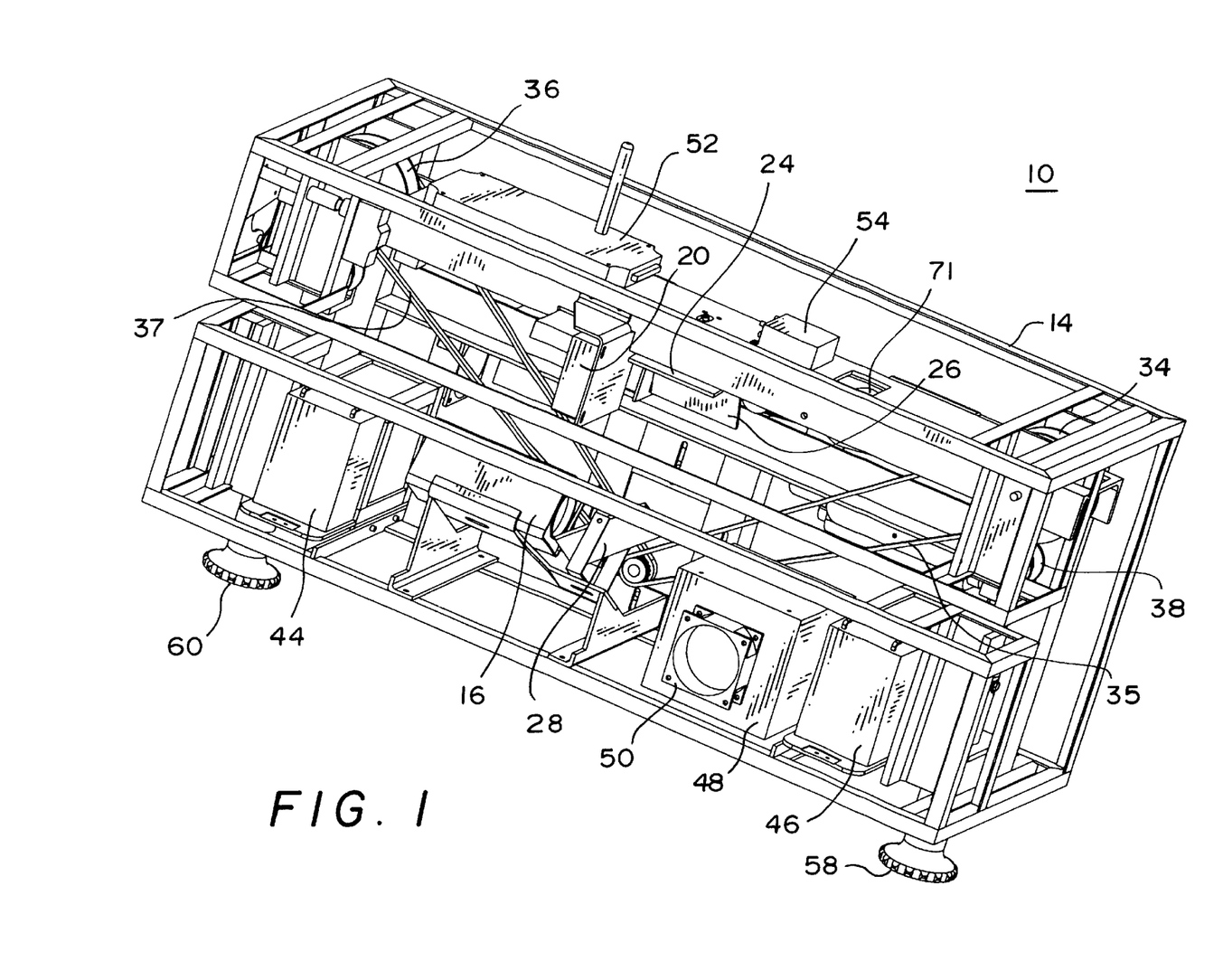
FIG. 1 is a perspective view of a cable and line inspection mechanism constructed in accordance with a preferred embodiment of the present invention.
Figure 2:
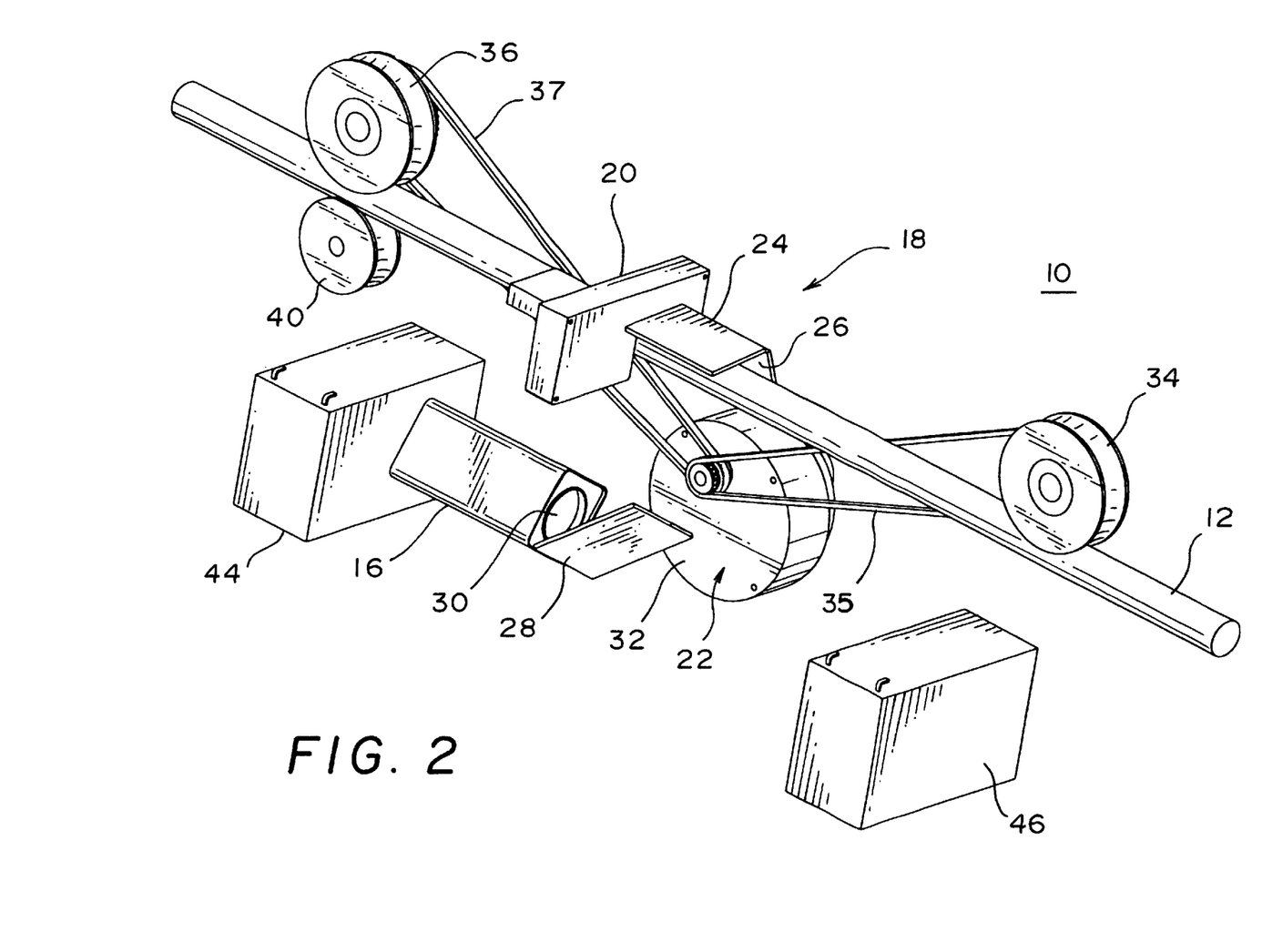
FIG. 2 is a schematic illustration showing a select number of the key elements in the cable and line inspection mechanism of FIG. 1.
Figure 6A:
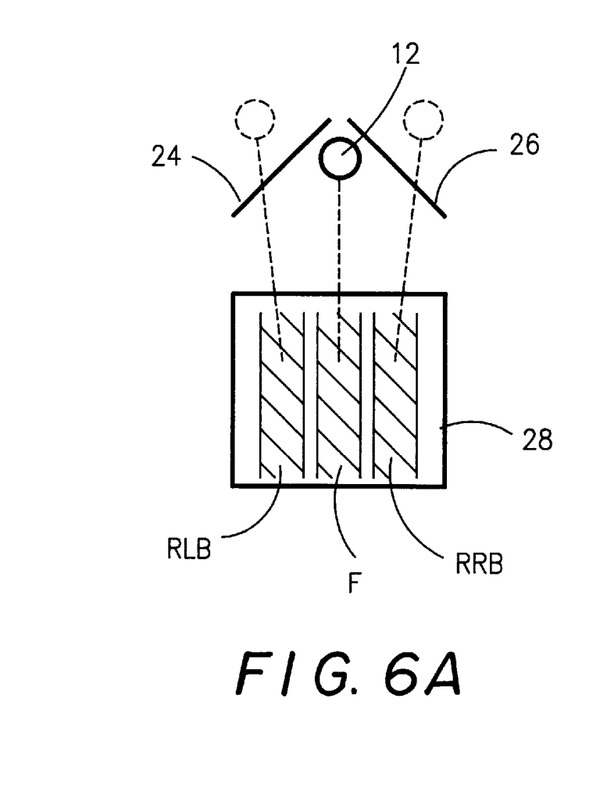
FIGS. 6A and 6B are schematic diagrams illustrating the operation of a minor assembly that is employed in the preferred embodiment to supply multiple images of a cable to be inspected to a video camera.
Figure 6B:
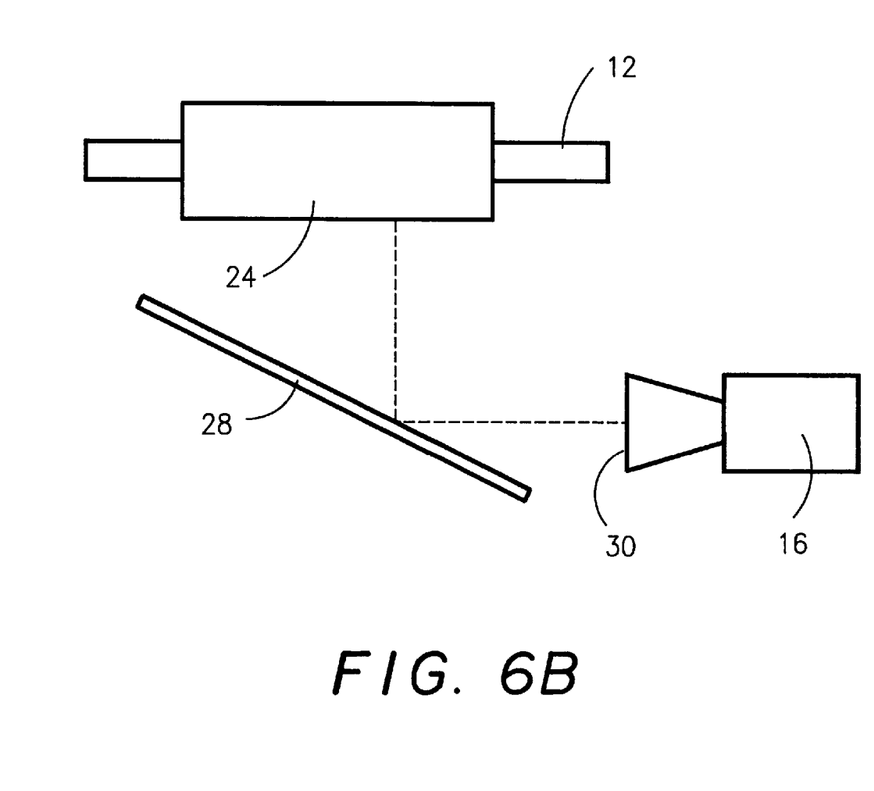

The mirror assembly 18 includes first and second mirrors 24 and 26 that are positioned adjacent to, and at an angle to, one another. A third mirror 28 is disposed adjacent a lens 30 of the video camera 16 at an angle thereto so that the camera 16 can be positioned parallel to a longitudinal axis of the cable 12 for packaging efficiency. It will be understood, however, that the third mirror could be left out if the camera 16 were positioned perpendicular to the cable 12. The first and second mirrors 24 and 26 are positioned so that they face portions of the cable 12 that are facing away from the third mirror 28, and thus could not otherwise be viewed by the camera 16. As illustrated by the schematic diagrams in FIGS. 6A and 6B, the mirror assembly 18 thus generates three side-by-side images of the cable or line 12 that are received by the lens 30 of the video camera 16. These three images, which include a reflected left backside view (RLB), a front side view F and a reflected right backside view (RRB), provide a view of the entire circumference of the cable 12.

The drive system 22 includes a drive motor 32 for rotating first and second drive wheels 34 and 36 that are positioned in engagement with the cable 12 when the frame 14 is mounted thereon. First and second drive chains 35 and 37 couple the drive motor 32 to the first and second drive wheels 34 and 36, respectively. Rotation of the drive wheels 34 and 36 causes movement of the CLIM 10 along the length of the cable 12. First and second corresponding tension wheels 38 and 40 are also provided which insure positive engagement of the drive wheels 34 and 36 with the cable 12, and at the same time act to secure the CLIM 10 to the cable 12.

Additional elements of the CLIM 10 are illustrated in FIGS. 1 and 3–5. Many of these elements comprise frame members, brackets and the like which are conventional in nature, and need not be discussed in detail. However, a number of the elements warrant further discussion. A number of electrical components, and/or housings therefore, are shown that are also illustrated in the circuit diagram of FIG. 7 to be discussed later. These include first and second battery packs 44 and 46 for powering the CLIM 10; a processor unit housing 48 for housing the CLIM's processor unit and other circuit cards; a cooling fan 48 for the circuit cards; an RF transceiver 52; a video transceiver 54; and a video storage device 56 (e.g., a VCR). A pair of limit switches 57 are mounted on the front of the frame 14 that sense when the CLIM 10 contacts a structure at an end of a cable being inspected, so that the CLIM's direction of travel can be reversed.

Additional elements of the CLIM 10 are illustrated in FIGS. 1 and 3–5. Many of these elements comprise frame members, brackets and like which are conventional in nature, and need not be discussed in detail. However, a number of the elements warrant further discussion. A number of the electrical components, and/or housings therefore, are shown that are also illustrated in the circuit diagram of FIG. 7 to be discussed later. These include first and second battery packs 44 and 46 for powering the CLIM 10; a processor unit housing 48 for housing the CLIM's processor unit and other circuit cards; a cooling fan 50 for the circuit cards; an RF transceiver 52; a video transceiver 54; and a video storage device 56 (e.g., a VCR). A pair of limit switches 57 are mounted on the front of the frame 14 that sense when the CLIM 10 contacts a structure at an end of a cable being inspected, so that the CLIM's direction of travel can be reversed.

Figure 3:
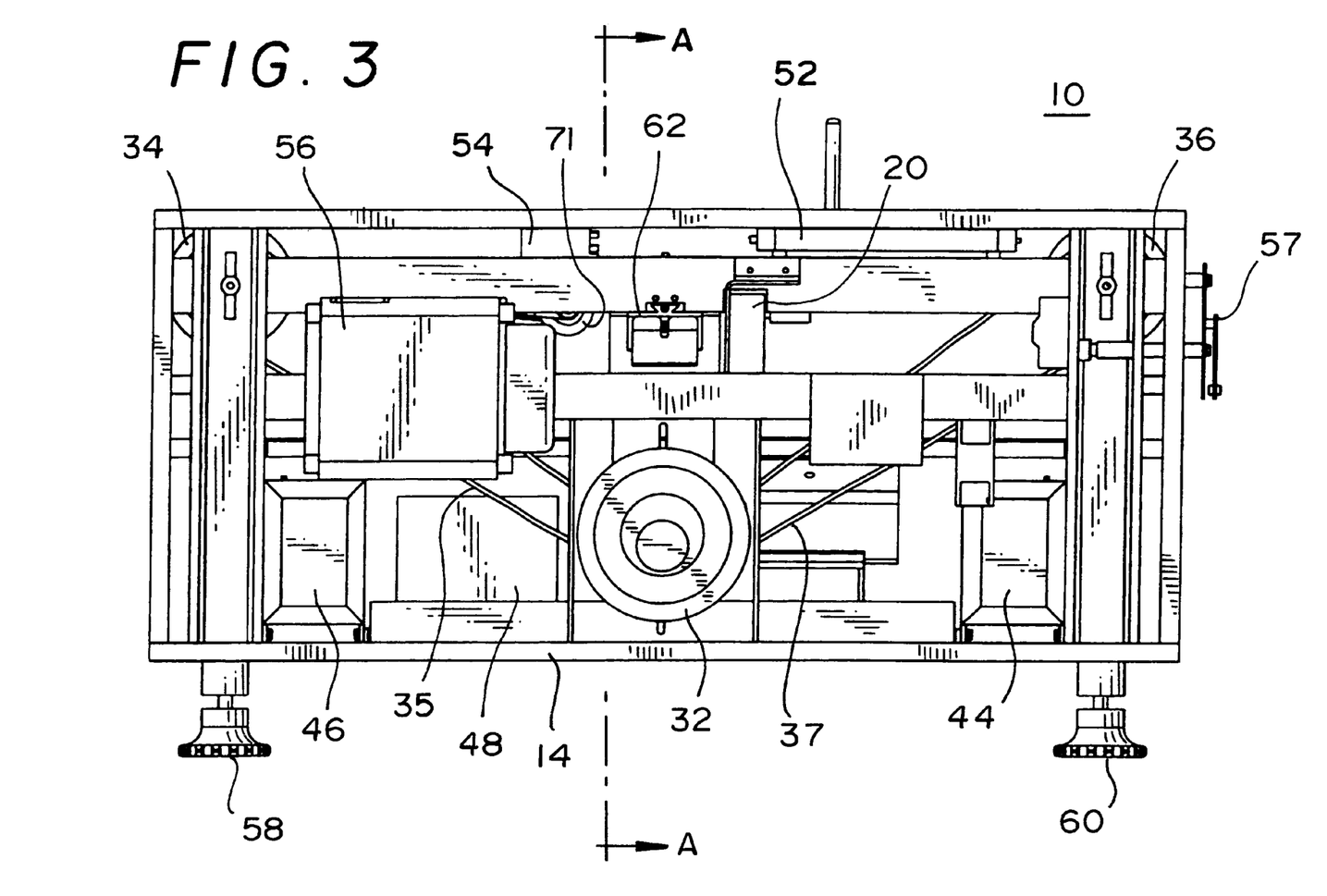
FIG. 3 is a back elevation of the cable and line inspection mechanism.
Figure 4:
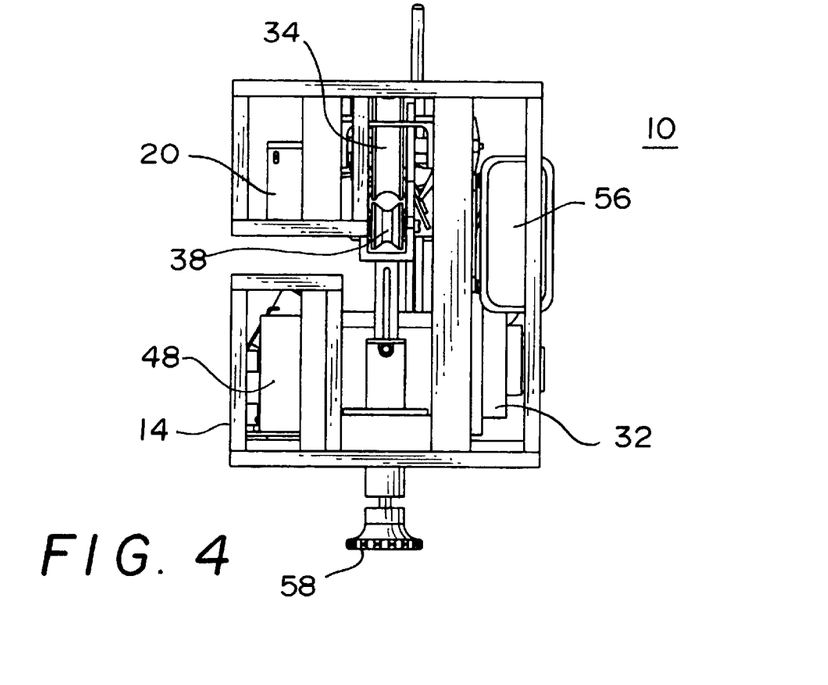
FIG. 4 is a right side view of the cable and line inspection mechanism.
Figure 5:
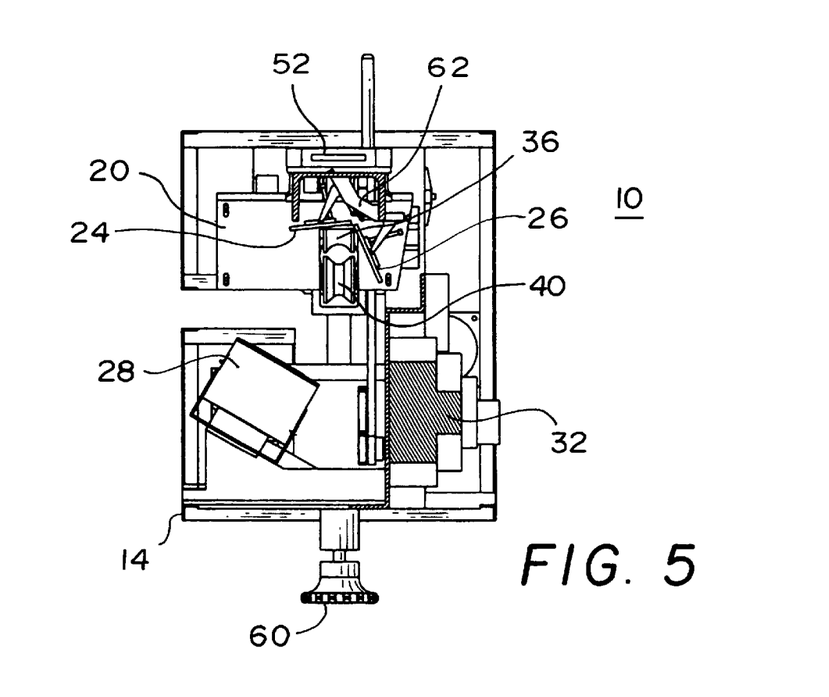
FIG. 5 is a right side sectional view of the cable and line inspection mechanism taken along line A—A of FIG. 3.

A number of notable mechanical elements include first and second spring loaded tension rod and knob assemblies 58 and 60 for releasing the tension on the tension wheels 38 and 40 to facilitate mounting and removal of the CLIM 10 on and from the cable 12. The mirror assembly 18 also includes a mount assembly 62, as illustrated in FIGS. 3 and 5, for securing the assembly 18 to the frame 14.

Figure 7:
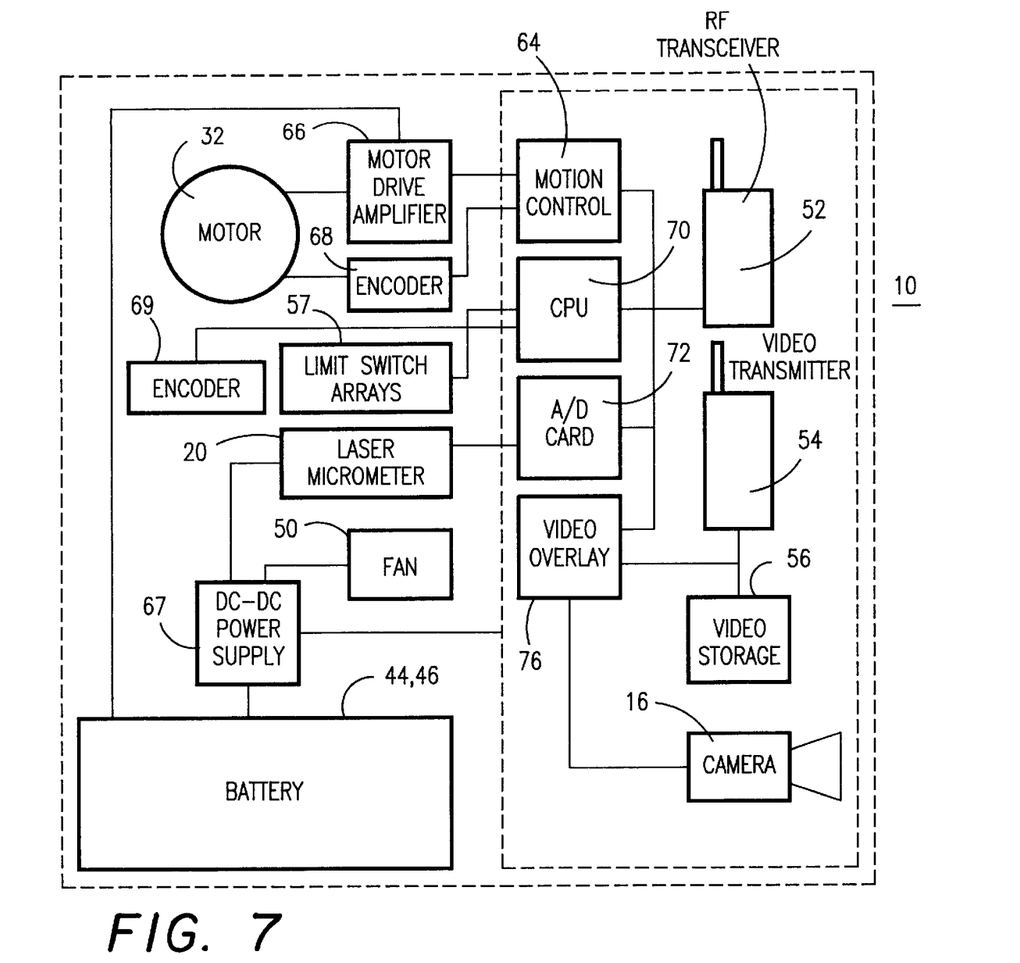
FIG. 7 is a block diagram of electronic circuitry employed in the cable and line inspection mechanism.

The electronic circuitry for the CLIM 10 is illustrated in the block diagram of FIG. 7. All of the components in the circuitry are mounted on the frame 14, and many of them are contained in the processor unit housing 48. A motion control circuit 64 controls the drive motor 32 through a motor drive amplifier 66. Power is supplied to the motor drive amplifier from the battery packs 44 and 46. A DC-DC power supply 67 converts voltage from the batteries 44 and 46 to the appropriate level for powering the laser micrometer 20, the cooling fan 50 and the remaining electronics to be discussed.

A first position encoder 68 mounted on the motor 32 provides motor speed data as feedback to the motion control circuit 64 so that the speed of the motor 32 can be accurately controlled. A second position encoder 69 generates cable position data that is fed to a central processor unit (CPU) 70 (which includes a memory, not shown), and indicates the present distance of the CLIM 10 from its starting position. The second position encoder 69 generates this data by monitoring the rotation of a wheel 71 that is held in engagement with the cable 12 (the wheel 71 is partially visible in FIGS. 1 and 3). The laser micrometer 20 generates an analog signal that is proportional to the measured diameter of the cable 12. This signal is fed to an A/D converter card 72 that digitizes the signal, and transfers it to the CPU 70. Battery condition data is also fed to the CPU 70.

Figure 8:
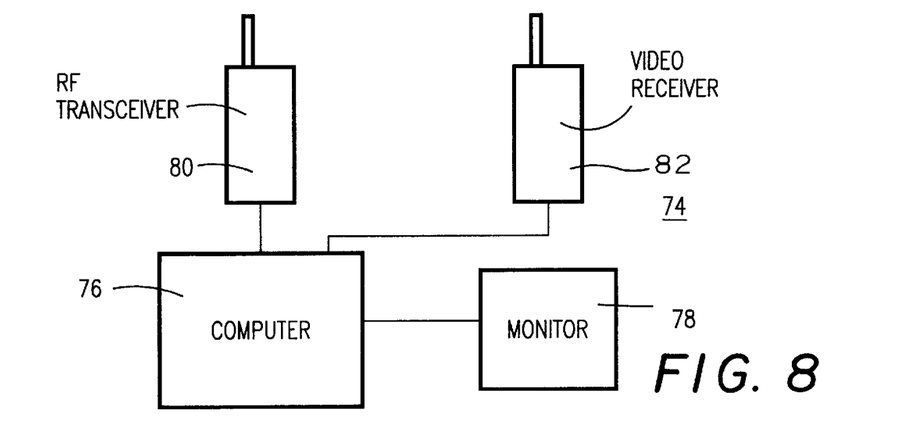
FIG. 8 is a block diagram of electronic circuitry employed in a remote control unit for controlling operation of the cable and line inspection mechanic

The cable position data, cable diameter data and battery condition data are transmitted by the RF transceiver 52 to a remote control station 74 illustrated in FIG. 8. In addition, all of this data is fed to a video overlay circuit 76 that is interfaced between the camera 16 and the VCR 56, and overlays the position, diameter and battery condition data on the generated video image of the cable 12. The video image with the added information is recorded by the VCR 56, stored in a text fie in the memory of the CPU 70, and is also transmitted to the remote control station 74 by the video transmitter 54.

As illustrated in FIG. 8, the remote control station 74 is comprised of a conventional computer 76, including a monitor 78, which is interfaced to a second RF transceiver 80 and a video receiver 82. The computer 76 sends commands and other data to the CPU 70 in the CLIM 10, and receives the position, cable diameter and battery condition data from the CPU 70, with the RF transceiver 80. The video receiver 82 receives video images of the cable 12.

In operation, the CLIM 10 is mounted with the drive wheel/tension wheel pairs (34,38) and (36,40) at one end of a cable or fine to be inspected. Commands are sent from the remote control station 74 to the CPU 70 in the CLIM 10 to initiate operation of the CLIM's components, including the video camera 16, laser micrometer 20 and motion control circuit 64. The motion control circuit 64 commands the drive motor 32 to start, and the CLIM 10 begins traveling along the length of the cable or line. As this movement continues, the video camera 16 generates images of the cable or line, with the cable diameter and position data overlaid thereon by the overlay circuit 76. Once the CLIM 10 reaches the end of the cable or line as detected by the limit switches 57, the CLIM 10 reverses direction, and travels at maximum speed back to the starting point where it is retrieved. The video images are then inspected for failures or flaws in the cable, such as frayed or jammed strands, bird caging, stretching and corrosion. The position information on the image provides quick identification of the location along the cable or line of any detected defects, while the diameter information provides an indication of whether cable stretching has occurred, since this will reduce the cable's diameter.

The video images of the cable can be viewed in real-time on the remote control station's monitor 78, and/or can be analyzed later by reviewing the videotape recorded by the VCR 56. It should be understood that if the later mode of operation is solely employed, the remote control station 74 is not necessary. This is because the CLIM 10 can be programmed to perform its inspection of the cable automatically upon being initiated by an inspection crew at the first end of the cable. The CLIM 10 will then travel along the cable, generating and storing video images thereof until the opposite end of the cable is reached. There, the limit switches 57 will trigger reversal of the drive motor 32, and return of the CLIM 10 to the starting point for retrieval by the inspection crew. In the control station mode of operation, the cable position data enables the inspection crew to send the CLIM 10 back to potential problem spots for a closer inspection of the cable 12.

Although the invention has been disclosed in terms of a preferred embodiment, and variations thereon, it will be understood that additional modifications and variations could be made thereto without departing from the scope of the invention as defined in the following claims.

What is claimed is:

1. An apparatus for systematically inspecting an outer circumferential surface of a generally linear extending cable or line during movement of the apparatus in a direction parallel to the generally linear cable or line to be inspected, comprising:
   a) a frame enclosing at least a portion of the cable or line to be inspected;
   b) a video camera mounted on said frame for generating a video image of the cable or line to be inspected, said camera including a lens:
   c) a mirror assembly mounted on said frame and including at least first and second mirrors, jointly positioned for projecting a plurality of side-by-side images of the cable or line to be inspected on said camera lens, with each of said images being of a different portion of the outer circumference of the cable or line to be inspected, thereby providing said camera lens with views of the entire outer circumference of the cable or line to be inspected including those portions of the circumference facing away from said camera lens; and
   d) a drive system for systematically driving said frame along a length of the outer circumference of the cable or line to be inspected as said video camera generates images thereof, said drive system including means for releasably mounting said frame on the cable or line to be inspected.

2. The apparatus of claim 1, further comprising a laser micrometer mounted on said frame for measuring a diameter of a cable or line to be inspected.

3. The apparatus of claim 1, wherein said camera is mounted on said frame and extends in a direction parallel to a longitudinal axis of the cable or line to be inspected, and said apparatus further includes a third mirror disposed adjacent said camera at an angle thereto for reflecting images received from said first and second mirrors at a right angle into said camera lens.

4. The apparatus of claim 1, wherein said drive system further comprises:
   1) a drive motor;
   2) a motion control circuit for controlling said drive motor;
   3) first and second drive wheels for engaging a cable or line to be inspected;
   4) first and second tension wheels positioned opposite said first and second drive wheels, respectively, for urging a cable or line to be inspected into engagement with said first and second drive wheels, respectively; and
   5) first and second chains for coupling said drive motor to said first and second drive wheels, respectively;
   whereby, actuation of said drive motor moves said apparatus along a length of a cable or line to be inspected through rotation of said first and second drive wheels, and said first and second tension wheels, in combination with said first and second drive wheels, secure said frame to a cable or line to be inspected.

5. The apparatus of claim 1, further comprising a position encoder mounted on said frame for determining a position of said apparatus along a length of a cable to be inspected.

6. The apparatus of claim 1, further comprising:
   e) a processor unit interfaced to said drive system for controlling operation thereof.

7. The apparatus of claim 6, further comprising:
   f) a video transmitter mounted on said frame for transmitting video signals generated by said camera;
   g) a first RF transceiver mounted on said frame for facilitating communication of data and commands to and from said processor unit; and
   h) a remote control station including:
      1) a computer;
      2) a video receiver interfaced to said computer for receiving video signals from said video transmitter; and
      3) a second RF transceiver for communicating with said first RF transceiver, said second RF transceiver being interfaced to said computer.

8. The apparatus of claim 1, further including a video overlay circuit interfaced to said video camera and said video transmitter for overlaying identification information on a video image generated by said camera.

9. The apparatus of claim 1, further comprising a video storage device mounted on said frame for receiving and storing video images generated by said camera.

10. The apparatus of claim 1, further comprising a power supply disposed on said frame for supplying power to said camera and said drive system.

11. The apparatus of claim 1, further including switch means mounted on an end of said frame for sensing when said frame contacts a structure at an end of a cable or line to be inspected, and causing said drive system to reverse direction of movement of said frame, and return said frame to a starting point.

12. An apparatus for systematically inspecting an outer circumferential surface of a generally linear extending cable or line during movement of the apparatus in a direction parallel to the cable or line to be inspected, comprising:
   a) a frame enclosing a least a portion of the cable or line to be inspected;
   b) a video camera mounted on said frame for generating a video image of the cable or line to be inspected, said camera including a lens;
   c) a mirror assembly mounted on said frame for projecting a plurality of side-by-side images of the cable or line to be inspected on said camera lens, with each of said images being of a different portion of the outer circumference of the cable or line to be inspected, thereby providing said camera lens with views of the entire outer circumference of the cable or line to be inspected including those portions of the outer circumference facing away from the camera lens;
   d) a drive system for physically engaging opposite sides of the cable or line to be inspected and systematically driving said frame parallel to the cable or line to be inspected as said video camera generates images thereof, said drive system including means for mounting said frame on the cable or line to be inspected, said means for mounting including two pairs of spaced-apart wheels frictionally engaging opposite sides of the outer circumference of the generally linear cable or line to be inspected;
   e) a laser micrometer mounted on said frame for determining a position of said apparatus along a length of the cable or line to be inspected;

f) a position encoder mounted on said frame for determining a position of said apparatus along a length of the cable or line to be inspected;

g) a processor unit mounted on said frame, and interfaced to said drive system, said micrometer and said encoder for controlling operation thereof and receiving data therefrom; and h) a power supply disposed on said frame for supplying power to said camera, said drive system, said micrometer, said encoder and said processor.

13. The apparatus of claim 12, wherein said mirror assembly includes first and second mirrors for directing to said camera lens, reflected images of first and second portions of a cable or line to be inspected that face away from said camera lens.

14. The apparatus of claim 13, wherein said camera is mounted in said frame in a direction parallel to a longitudinal axis of a cable or line to be inspected, and said apparatus further includes a third mirror disposed adjacent said camera lens at an angle thereto for reflecting images received from said first and second mirrors at a right angle into said camera lens.

15. The apparatus of claim 12, wherein said drive system further comprises:

1) a drive motor;

2) a motion control circuit for controlling said drive motor, said motion control circuit being interfaced to said processor unit;

3) first and second drive wheels for engaging a cable or line to be inspected;

4) first and second tension wheels positioned opposite said first and second drive wheels, respectively, for urging a cable or line to be inspected into engagement with said first and second drive wheels, respectively; and 5) first and second chains for coupling said drive motor to said first and second drive wheels, respectively;

whereby, actuation of said drive motor moves said apparatus along a length of a cable or line to be inspected through rotation of said first and second drive wheels, and said first and second tension wheels, in combination with said first and second drive wheels, secure said frame to a cable or line to be inspected.

16. The apparatus of claim 12, further comprising:

i) a video transmitter mounted on said frame for transmitting video signals generated by said camera;

j) a first RF transceiver mounted on said frame for facilitating communication of data and commands to and from said processor unit; and k) a remote control station including:
1) a computer;
2) a video receiver interfaced to said computer for receiving video signals from said video transmitter; and
3) a second RF transceiver for communicating with said first RF transceiver, said second RF transceiver being interfaced to said computer.

17. The apparatus of claim 12, further including switch means mounted on an end of said frame and interfaced to said processor unit for sensing when said frame contacts a structure at an end of a cable or line to be inspected, and causing said motor to reverse direction and return said frame to a starting point.

18. The apparatus of claim 12, further including a video overlay circuit interfaced to said video camera for overlaying information on a video image generated by said camera, said information including cable diameter data generated by said micrometer, and cable position data generated by said position encoder.

19. The apparatus of claim 12, further comprising a video storage device mounted on said frame for receiving and storing video images generated by said camera.

* * * * *

UNITED STATES PATENT AND TRADEMARK OFFICE
CERTIFICATE OF CORRECTION

PATENT NO. : 6,512,536 B1
DATED : January 28, 2003
INVENTOR(S) : Terence J. Ross It is certified that error appears in the above-identified patent and that said Letters Patent is hereby corrected as shown below:

<u>Title page,</u>
Item [57], ABSTRACT,
Line 3, change "cable=s length" to -- cable's length. --
Line 6, change "cable=s diameter" to -- cable's diameter. --

Signed and Sealed this

Fifteenth Day of July, 2003

JAMES E. ROGAN
*Director of the United States Patent and Trademark Office*